United States Patent [19]

Franck-Neumann et al.

[11] 4,410,721
[45] Oct. 18, 1983

[54] PROCESS FOR THE PREPARATION OF CYCLOPROPENE INTERMEDIATES

[75] Inventors: Michel Franck-Neumann, Strasbourg; Michel Miesch, Mulhouse, both of France

[73] Assignee: Roussel Uclaf, Paris, France

[21] Appl. No.: 284,125

[22] Filed: Jul. 16, 1981

Related U.S. Application Data

[62] Division of Ser. No. 182,062, Aug. 28, 1980, Pat. No. 4,299,973.

[30] Foreign Application Priority Data

Sep. 10, 1979 [FR] France .................. 79 22559

[51] Int. Cl.$^3$ .................................. C07C 67/303
[52] U.S. Cl. .................. 560/124; 204/158 R
[58] Field of Search .............. 560/124; 204/158 R

[56] References Cited

U.S. PATENT DOCUMENTS

| | | | |
|---|---|---|---|
| 3,282,948 | 11/1966 | Matsui | 560/124 |
| 3,527,769 | 9/1970 | Matsui | 560/124 |
| 3,699,146 | 10/1972 | Gensler | 560/124 |
| 3,989,654 | 11/1976 | Honda | 560/124 |

4,233,129 11/1980 Franck-Neumann ........... 204/158 R

*Primary Examiner*—Michael L. Shippen
*Attorney, Agent, or Firm*—Hammond & Littell, Weissenberger and Muserlian

[57] ABSTRACT

A novel cyclopropene-carboxylate of the formula

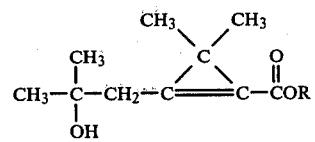

wherein R is alkyl of 1 to 6 carbon atoms and their preparation and a process using the compounds of formula I to obtain cis compounds of the formula

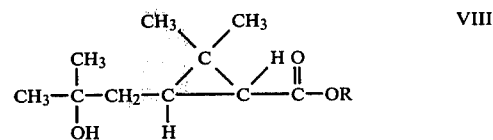

2 Claims, No Drawings

PROCESS FOR THE PREPARATION OF CYCLOPROPENE INTERMEDIATES

PRIOR APPLICATION

This application is a divisional application of copending, commonly assigned U.S. patent application Ser. No. 182,062, filed Aug. 28, 1980, now U.S. Pat. No. 4,299,973.

STATE OF THE ART

Copending, commonly assigned U.S. patent application Ser. No. 59,291, filed July 20, 1979, now U.S. Pat. No. 4,233,129, describes alkyl esters of dl cis chrysanthemic acid having the formula

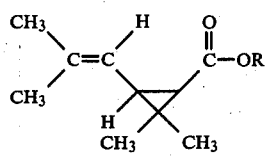

wherein R is an alkyl having from 1 to 6 carbon atoms.

OBJECTS OF THE INVENTION

It is an object of the invention to provide the novel cyclopropenes of formula I and a process for their preparation.

It is a further object of the invention to provide a novel process for the preparation of cis compounds of formula VII.

These and other objects and advantages of the invention will become obvious from the following detailed description.

THE INVENTION

The novel compounds of the invention are cyclopropene-carboxylates of the formula

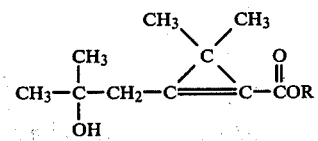

wherein R is alkyl of 1 to 6 carbon atoms.

Examples of R are methyl, ethyl, propyl, isopropyl, linear and branched butyl, pentyl and hexyl. The preferred compound is ethyl 3,3-dimethyl-2-(2-hydroxy-2-methyl-propyl)-1-cyclopropene-1-carboxylate.

The process of the invention for the preparation of compounds of formula I comprises reacting a compound of the formula

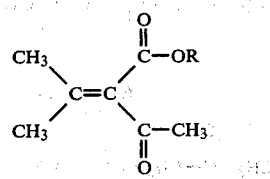

wherein R has the above definition with a strong base and then with an organolithium and reacting the resulting product with acetone to obtain a compound of the formula

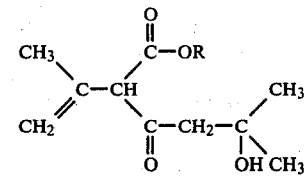

reacting the latter with a basic agent or an acid agent to isomerize the compound to a compound of the formula

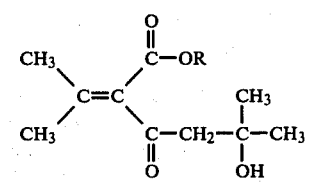

and reacting the latter with hydrazine in acetic acid to obtain a compound of the formula

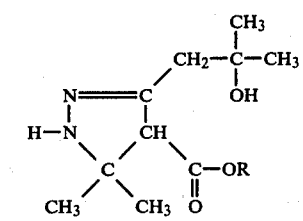

and treating the latter with an oxidation agent in a heterogenous phase to obtain a compound of the formula

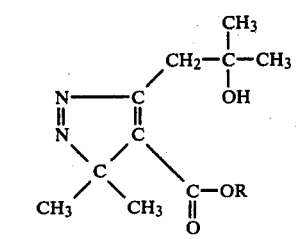

and subjecting the latter to irradiation to obtain a compound of formula I.

In a preferred mode of the process, the compound of formula II is reacted with sodium hydride or sodium amide and then with methyl lithium or butyl lithium the compound of formula III is isomerized with a basic alumina or other bases such as alkali metal hydroxides or alkali metal carbonate or an acid agent, the oxidation agent in a heterogenous phase is manganese dioxide or nickel peroxide and the irradiation is effected with a mercury vapor lamp.

The compounds of formula I are useful for the preparation of a cis compound of the formula which are precursors of dl cis chrysanthemic acid by reacting a compound of formula I with a reducing agent selected from the group consisting of hydrogen in the presence of nickel boride, palladium or platinum and diimide.

The compounds of formula VII are described in Japanese published patent application No. 2095/68 and it is known to subject the compound of formula VII to hydrolysis to remove the ester group and to deshydration of the lateral chain to form dl cis chrysanthemic acid which is of interest to produce cyclopropane carboxylic acids with a dihalovinyl side chain whose esters are known to possess remarkable insecticidal properties [French Pat. Nos. 2,185,612 and 2,240,914].

The process of the invention permits the preparation of dl cis chrysanthemic acid in excellent yields with a reduced number of steps.

In the following examples there are described several preferred embodiments to illustrate the invention. However, it should be understood that the invention is not intended to be limited to the specific embodiments.

EXAMPLE 1

Ethyl 3,3-dimethyl-2-(2-hydroxy-2-methyl-propyl)-1-cyclopropene-1-carboxylate

STEP A: Ethyl 5-hydroxy-5-methyl-2-(1-methyl-ethenyl)-3-oxo-hexanoate 3.00 g of ethyl 2-(1-methyl-ethylidene)-3-oxo-butanoate [described in Helv. Chim. Act., Vol. 54 (1971), p. 1797] were added dropwise at room temperature to a suspension of 860 mg of sodium hydride as a 50% mineral oil suspension in 50 ml of tetrahydrofuran and the mixture was refluxed for one hour and then cooled to room temperature. 13 ml of a solution of 1.6 M of butyl-lithium in hexane were added to the mixture at 0° C. and the mixture was stirred at 0° C. for 30 minutes. The mixture was cooled to −10° C. and 1.60 ml of acetone were added thereto. The mixture was poured into water and the mixture was extracted with ether. The ether phase was washed with aqueous saturated sodium chloride solution, dried over magnesium sulfate and evaporated to about 100 ml to obtain a solution of ethyl 5-hydroxy-5-methyl-2-(1-methyl-ethenyl)-3-oxo-hexanoate and its isomer, ethyl 5-hydroxy-5-methyl-2-(1-methyl-ethenyl)-3-oxo-hexanoate.

STEP B: Ethyl 5-hydroxy-5-methyl-2-(1-methylethylidene)-3-oxo-hexanoate 15 g of basic alumina were added to the solution of Step A and the mixture was stirred overnight and was then filtered. The filtrate was evaporated to dryness and the residue was chromatographed over silica gel. Elution was with a 4-6 ether-petroleum ether (b.p.=40° to 60° C.) mixture. Elution with a 1-1 ether-petroleum ether mixture eliminated the starting compound and elution with an 8-2 ether-petroleum ether mixture yielded 1.85 g of ethyl 5-hydroxy-5-methyl-2-(1-methyl-ethylidene)-3-oxo-hexanoate.

STEP C: Ethyl 4,5-dihydro-5,5-dimethyl-3-(2-hydroxy-2-methyl-propyl)-[1H]-pyrazole-4-carboxylate 500 mg of the product of Step B were added to 3 ml of acetic acid and 121 mg of hydrazine hydrate and the temperature rose spontaneously to 40° C. The acetic acid was distilled by heating the mixture up to 180° C. during which the majority of the acetic acid was removed. The mixture was cooled and water was added thereto. The mixture was extracted with chloroform and the organic phase was dried over magnesium sulfate and evaporated to dryness to obtain 520 mg of ethyl 4,5-dihydro-5,5-dimethyl-3-(2-hydroxy-2-methyl-propyl)-[1H]-pyrazole-4-carboxylate in the form of a liquid.

STEP D: Ethyl 3,3-dimethyl-5-(2-hydroxy-2-methyl-propyl)-[3H]-pyrazole-4-carboxylate A suspension of 1.5 g of manganese dioxide in 50 ml of methylene chloride was stirred under an inert gas for 15 minutes and 200 mg of the product of Step C were added. The mixture was stirred for one hour and was filtered. The filtrate was evaporated to dryness to obtain 185 mg of ethyl 3,3-dimethyl-5-(2-hydroxy-2-methyl-propyl)-[3H]-pyrazole-4-carboxylate.

STEP E: Ethyl 3,3-dimethyl-2-(2-hydroxy-2-methyl-propyl)-cyclopropane-1-carboxylate 350 mg of the product of Step D were dissolved in 100 ml of ethyl acetate and an inert gas was bubbled therethrough for 15 minutes and the solution was then irridated with a mercury vapor lamp. After 10 minutes, 33 ml of nitrogen were disengaged and the solution was evaporated to dryness to obtain 290 mg of ethyl 3,3-dimethyl-2-(2-hydroxy-2-methyl-propyl)-cyclopropane-1-carboxylate.

EXAMPLE 2

Ethyl cis 2,2-dimethyl-3-(2-hydroxy-2-methyl-propyl)-cyclopropane-1-carboxylate

A mixture of a solution of the compound of Example 1 in ethyl acetate and 90 mg of 5% palladized carbon were placed in a hydrogenation apparatus and the mixture was stirred under a slight hydrogen pressure for 30 minutes. The mixture was filtered and the filtrate was evaporated to dryness. The residue was chromatographed over silica gel and was eluted with a 3-7 ether-hexane mixture to obtain 275 mg of ethyl cis 2,2-dimethyl-3-(2-hydroxy-2-methyl-propyl)-cyclopropane-1-carboxylate.

Various modifications of the products and processes of the invention may be made without departing from the spirit or scope thereof and it is to be understood that the invention is to be limited only as defined in the appended claims.

We claim:

1. A process for the preparation of a compound of the formula $$CH_3-\underset{\underset{OH}{|}}{\overset{\overset{CH_3}{|}}{C}}-CH_2-C\overset{\overset{CH_3\diagdown\diagup CH_3}{C}}{\underset{}{\diagup\diagdown}}C-COR$$

wherein R is alkyl of 1 to 6 carbon atoms comprising reacting a compound of the formula

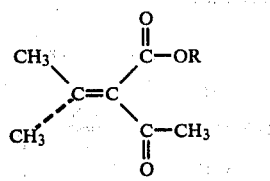

wherein R has the above definition with a strong base and then with an organolithium and reacting the resulting product with acetone to obtain a compound of the formula

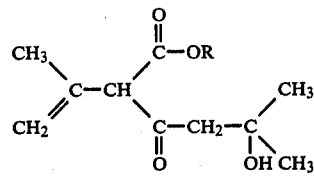

reacting the latter with a basic agent or an acid agent to isomerize the compound to a compound of the formula

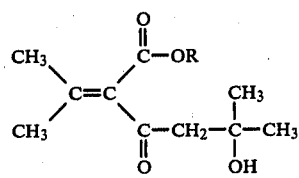

and reacting the latter with hydrazine in acetic acid to obtain a compound of the formula

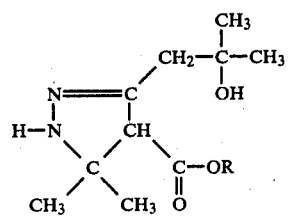

and treating the latter with an oxidation agent in a heterogenous phase to obtain a compound of the formula

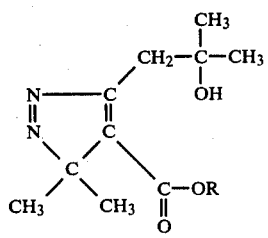

and subjecting the latter to irradiation to obtain the desired compound.

2. A process for the preparation of a cis compound of the formula

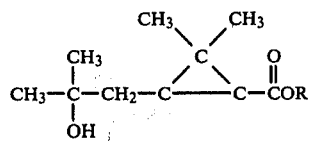

wherein R is alkyl of 1 to 6 carbon atoms comprising reacting a compound of the formula

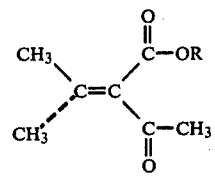

wherein R has the above definition with a strong base and then with an organolithium and reacting the resulting product with acetone to obtain a compound of the formula

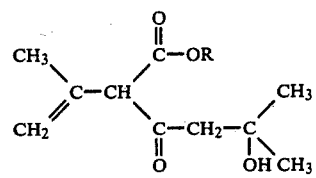

reacting the latter with a basic agent or an acid agent to isomerize the compound to a compound of the formula

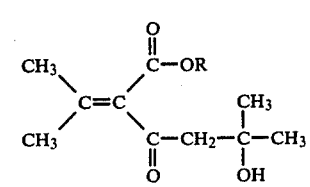

and reacting the latter with hydrazine in acetic acid to obtain a compound of the formula

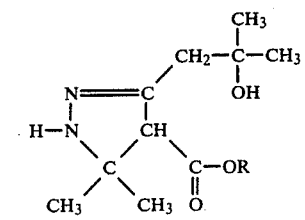

and treating the latter with an oxidation agent in a heterogenous phase to obtain a compound of the formula

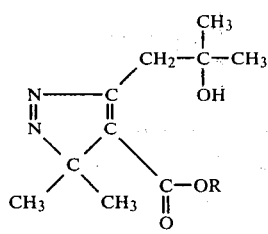
subjecting the latter to irradiation to obtain a cis compound of the formula
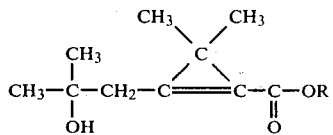
and reacting the latter with a reducing agent selected from the group consisting of hydrogen in the presence of nickel boride, palladium or platinum and diimide to obtain the desired compound.
* * * * *